United States Patent
Ikeda et al.

(10) Patent No.: US 6,547,954 B2
(45) Date of Patent: *Apr. 15, 2003

(54) BIOSENSOR AND METHOD FOR QUANTITATING BIOCHEMICAL SUBSTRATE USING THE SAME

(75) Inventors: Shin Ikeda, Katano (JP); Tomohiro Yamamoto, Neyagawa (JP); Toshihiko Yoshioka, Hirakata (JP); Shiro Nankai, Hirakata (JP); Shigeki Joko, Matsuyama (JP); Junko Iwata, Ehime-ken (JP)

(73) Assignee: Matsushita Electric Industrial Co., Ltd., Kadoma (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/232,320

(22) Filed: Jan. 18, 1999

(65) Prior Publication Data

US 2001/0052472 A1 Dec. 20, 2001

Related U.S. Application Data

(63) Continuation of application No. 08/812,602, filed on Mar. 7, 1997, now Pat. No. 5,922,188.

(30) Foreign Application Priority Data

Mar. 12, 1996 (JP) .............................................. 8-054594

(51) Int. Cl.[7] ........................................... G01N 27/327
(52) U.S. Cl. ............................... 205/777.5; 204/403.14
(58) Field of Search .......................... 204/403, 403.14, 204/403.11, 403.1, 403.9; 205/777.5, 792; 435/817

(56) References Cited

U.S. PATENT DOCUMENTS

| | | | |
|---|---|---|---|
| 4,857,167 A | | 8/1989 | Bashkin et al. .............. 204/435 |
| 5,512,159 A | * | 4/1996 | Yoshioka et al. ........... 204/403 |
| 5,516,644 A | * | 5/1996 | Yamauchi et al. ........... 435/7.9 |
| 5,922,188 A | * | 7/1999 | Ikeda et al. .............. 205/777.5 |

FOREIGN PATENT DOCUMENTS

| | | | |
|---|---|---|---|
| CA | 2068475 | 2/1996 | |
| EP | 0078636 | 5/1983 | .......... G01N/27/30 |
| EP | 0390390 | 10/1990 | .......... G01N/27/416 |
| JP | 299851 | 4/1990 | .......... G01N/27/327 |
| JP | 2240555 | 9/1990 | .......... G01N/27/327 |
| JP | 3202764 | 9/1991 | .......... G01N/27/327 |
| JP | 5256812 | 10/1993 | .......... G01N/27/327 |
| JP | 63316 | 1/1994 | .......... G01N/27/327 |

OTHER PUBLICATIONS

European Search Report for European patent application Ser. No. 97103966.4 dated Jul. 3, 1997.
Luong et al.; "Novel Approaches To The Development Of Mediated Biosensors And Enzyme Assay"; Nato ASI Series, Series E: Applied Sciences, Uses Of Immobilized Biological Compounds; vol. 253 (1993) pp. 211–230.
Office Action for dated Mar. 25, 1999 for Canadian patent application Ser. No. 2,199,657.

* cited by examiner

*Primary Examiner*—T. Tung
*Assistant Examiner*—Alex Noguerola
(74) *Attorney, Agent, or Firm*—Renner, Otto, Boisselle & Sklar

(57) ABSTRACT

A biosensor includes: an insulating substrate; an electrode system formed on the insulating substrate which has a working electrode and a counter electrode; and a reaction layer formed on the insulating substrate which contains an oxidoreductase and an electron acceptor. The electron acceptor is ferricinium ion derived from ferrocene electrolyte.

14 Claims, 2 Drawing Sheets

BIOSENSOR AND METHOD FOR QUANTITATING BIOCHEMICAL SUBSTRATE USING THE SAME

This application is a continuation of U.S. Ser. No. 08/812,602, filed Mar. 7, 1997, now U.S. Pat. No. 5,922,188.

BACKGROUND OF THE INVENTION

1. Field of the Invention

The present invention relates to a biosensor for quantitating a biochemical substrate (specific compound) contained in a sample liquid such as whole blood, urine, fruit juice and the like, with accuracy, speed and ease, and a method for quantitating a biochemical substrate by the biosensor. More particularly, the invention relates to a biosensor for electrochemically quantitating a concentration of a biochemical substrate in a sample liquid by reacting biochemical substrates such as glucose or cholesterol with an oxidoreductase which can react with specificity to the biochemical substrates, and a method for quantitating a biochemical substrate using thereof.

2. Description of the Related Art

Recently, biosensors have been proposed which can easily quantitate a specific compound (biochemical substrate) in a sample liquid such as a biological sample or a food without diluting or stirring the sample liquid.

For example, Japanese Laid-Open Patent Publication No. 3-202764 discloses a biosensor including an electrode system formed on an insulating substrate by screen printing or the like, a reaction layer formed on the electrode system and a space provided as a sample supply path by using a cover and a spacer. The reaction layer contains a hydrophilic polymer, an oxidoreductase, and an electron acceptor. Such a biosensor can quantitate the concentration of a biochemical substrate in a sample liquid as follows: First, the sample liquid is dropped on the space in the biosensor so as to be supplied to the reaction layer due to capillary phenomenon, thereby dissolving the reaction layer. This causes an enzyme reaction between the biochemical substrate in the sample liquid and the oxidoreductase in the reaction layer, whereby the electron acceptor in the reaction layer is reduced. After the completion of the enzyme reaction, the reduced electron acceptor is electrochemically oxidized, whereby the concentration of the biochemical substrate in the sample liquid is quantitated by an oxidation current value.

In the above-described biosensor, potassium ferricyanide is often used as the electron acceptor. Biosensors using potassium ferricyanide have excellent stability, can be produced at a low cost and thus appropriate in terms of mass production. However, the biosensor using potassium ferricyanide as the electron acceptor is associated with a second-order reaction velocity between the potassium ferricyanide and the oxidoreductase that is slower than that of a biosensor using an electron acceptor such as quinone derivatives or another metallic complex which is unstable or produced at a high cost. Accordingly, in the biosensor using potassium ferricyanide, an enzyme reaction takes substantially long time, thereby causing a problem of not being able to promptly quantitate the concentration of the biochemical substrate.

Additionally, several biosensors are known which employ ferrocene as an electron acceptor which has a faster second-order reaction velocity than those of potassium ferricyanide or derivatives thereof.

Japanese Laid-Open Patent Publication No. 2-240555 discloses a glucose sensor including a working electrode having a photo-curing resin film containing a ferrocene compound and a photo-curing resin film containing glucose oxidase sequentially provided on the surface of the working electrode. Japanese Laid-Open Patent Publication No. 2-99851 discloses a glucose sensor including a working electrode having a ferrocene compound-containing layer and a glucose oxidase-immobilized layer on the ferrocene compound-containing layer on the surface of the working electrode. In the above-mentioned biosensors, 1,1'-dimethyl ferrocene, ferrocene, i.e., bis(cyclopentadienyl)iron(II), vinyl ferrocene or the like is used as the ferrocene compound.

Japanese Laid-Open Patent Publication No. 5-256812 discloses a glucose sensor including a layer carrying glucose oxidase and a ferrocene compound on a working electrode and a means for maintaining a predetermined temperature in the vicinity of the working electrode. In this biosensor, ferrocene and/or derivatives thereof is used as the ferrocene compound.

However, any ferrocene compound used in the above-described glucose sensors normally exists as a reduced form. Therefore, in order to achieve electron transfer from the biochemical substrate to the working electrode by an enzyme reaction, the ferrocene compound needs to be converted into oxidized form on the electrode.

Japanese Laid-Open Patent Publication No. 6-3316 discloses a glucose sensor (a modified electrode) modified by a hydrophobic redox substance (e.g., a ferrocene) which has been ionized in advance in an aqueous solution, and a hydrophilic enzyme (e.g., glucose oxidase) on a surface of a conductive electrode. The glucose sensor is produced as follows: Ferrocene is electrolyzed in a phosphate buffer to form a solution containing ferricinium ions. Then, a glucose oxidase is added to the solution. The resultant mixed solution is applied to or electrodeposited on the surface of the conductive electrode.

However, the above-described modified electrode has a problem in that the phosphate ion and the ferricinium ion form an ion-like complex which renders the surface of the electrode inactive. Moreover, a step of electrolyzing ferrocene is required in order to produce the modified electrode. As a result, increased production time and increased cost are required.

SUMMARY OF THE INVENTION

According to one aspect of the present invention, a biosensor includes: an insulating substrate; an electrode system formed on the insulating substrate which has a working electrode and a counter electrode; and a reaction layer formed on the insulating substrate which contains an oxidoreductase and an electron acceptor. The electron acceptor is ferricinium ion derived from ferrocene electrolyte.

In one embodiment of the present invention, the ferrocene electrolyte is selected from the group consisting of ferrocenium hexafluorophosphate and ferrocenium tetrafluoroborate.

In one embodiment of the present invention, the reaction layer further comprises at least one surfactant.

In one embodiment of the present invention, the reaction layer further comprises at least one hydrophilic polymer.

In one embodiment of the present invention, the oxidoreductase is selected from the group consisting of glucose oxidase; glucose dehydrogenase; lactate oxidase; lactate dehydrogenase; uricase; cholesterol oxidase; a combination of cholesterol oxidase and cholesterol esterase; a combination of glucose oxidase and invertase; a combination of glucose oxidase, invertase and mutarotase; and a combination of fructose dehydrogenase and invertase.

According to another aspect of the present invention, a method is disclosed for quantitating the concentration of a biochemical substrate in a sample liquid by using a biosensor including an insulating substrate, an electrode system formed on the insulating substrate which has a working electrode and a counter electrode and a reaction layer provided on the insulating substrate which contains an oxidoreductase and an electron acceptor. The method includes the steps of: adding the sample liquid to the reaction layer; and detecting a response current value by applying a voltage between the working electrode and the counter electrode. The electron acceptor is ferricinium ion derived from ferrocene electrolyte.

Thus, the invention described herein makes possible the advantages of (1) providing a biosensor for promptly quantitating a concentration of a biochemical substrate with sufficiently short enzyme reaction time; (2) providing a biosensor for quantitating a concentration of a biochemical substrate with accuracy without deteriorating a detecting sensitivity; (3) providing a biosensor produced at sufficiently low cost; and (4) providing a method for quantitating a concentration of a biochemical substrate using the above-mentioned biosensor with accuracy and speed.

These and other advantages of the present invention will become apparent to those skilled in the art upon reading and understanding the following detailed description with reference to the accompanying figures.

DESCRIPTION OF THE PREFERRED EMBODIMENTS

Figure 1:
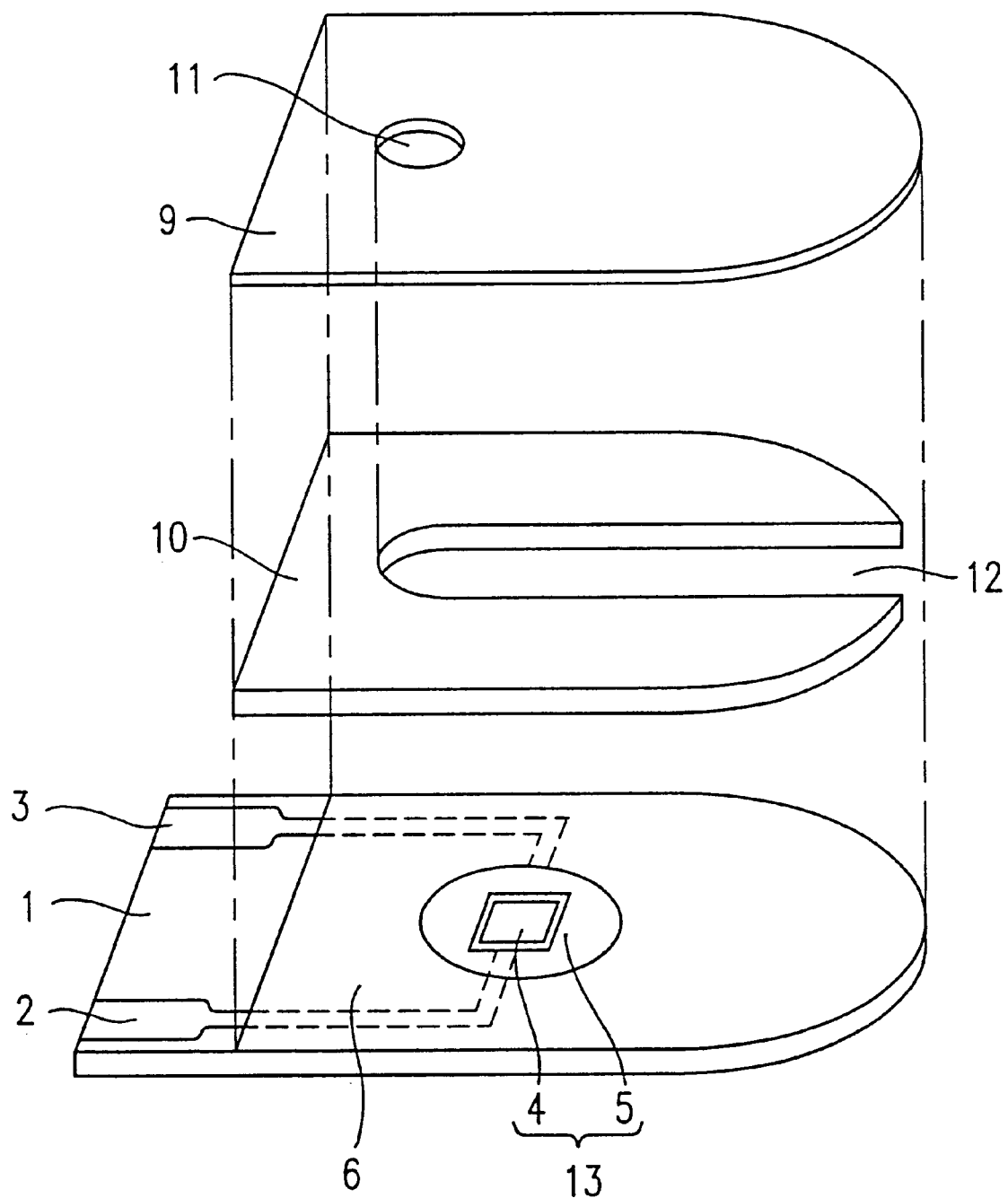
FIG. 1 is an exploded isometric view showing a biosensor according to an example of the present invention in which a reaction layer is omitted.

A biosensor according to the present invention includes an insulating substrate, an electrode system formed on the insulating substrate and a reaction layer disposed on the insulating substrate. The electrode system includes a working electrode and a counter electrode.

The insulating substrate may be a synthetic resin plate made, for example, of polyethylene terephthalate.

The electrode system including the working electrode and the counter electrode may be provided on the insulating substrate by a known method. For example, leads are formed on the insulating substrate. Then, the working electrode and the counter electrode are provided so as to be connected to the respective leads and insulated from each other. The leads and the electrodes may be made of any of the known conductive materials. Examples of the conductive material include carbon, silver, platinum, gold and palladium.

The reaction layer contains at least one oxidoreductase and at least one electron acceptor.

The electron acceptor used in the present invention is ferricinium ion derived from ferrocene electrolyte. The term "ferrocene electrolyte" herein refers to a salt which generates ferricinium ion ($[(C_5H_5)_2Fe]^+$) upon preparation of a solution with an oxidoreductase which will be described later. An anion composing the ferrocene electrolyte is not specifically limited. Preferred ferrocene electrolytes are, for example, ferrocenium hexafluorophosphate and ferrocenium tetrafluoroborate which are available from Aldrich Inc.

Although the concentration of the ferrocene electrolyte is not specifically limited, it is preferably about 1 to about 100 mM in the sample liquid when the reaction layer is dissolved in a sample liquid. When the concentration of the ferrocene electrolyte is smaller than 1 mM in the reaction layer, a measurable range of the concentration of a biochemical substrate may become extremely small. When the concentration of the ferrocene electrolyte exceeds 100 mM in the reaction layer, the biosensor may require an increased production cost and may cause fluctuation in a response current value and poor stability during the storage since the reaction layer can be broken during the formation thereof.

The oxidoreductase used in a conventional biosensor such as a glucose sensor, a cholesterol sensor, a lactic acid sensor, a uric acid sensor and a sucrose sensor can be used in the present invention. Examples of oxidoreductase include glucose oxidase (hereinafter, referred to as GOD), glucose dehydrogenase, lactose oxidase, lactose dehydrogenase, uricase, cholesterol oxidase (hereinafter, referred to as ChOD), cholesterol esterase (hereinafter, referred to as ChE), invertase, mutarotase and fructose dehydrogenase, and combinations thereof. In the case where a biosensor according to the present invention is a glucose sensor, GOD or glucose dehydrogenase may be used as the oxidoreductase. In the case where a biosensor according to the present invention is a lactic acid sensor, lactose oxidase or lactose dehydrogenase may be used as the oxidoreductase. In the case where a biosensor according to the present invention is a uric acid sensor, uricase may be used as the oxidoreductase. In the case where a biosensor according to the present invention is a cholesterol sensor, ChOD or a combination of ChOD and ChE may be used as the oxidoreductase. In the case where a biosensor according to the present invention is a sucrose sensor, a combination of GOD and invertase; a combination of GOD, invertase and mutarotase; or a combination of fructose dehydrogenase and invertase may be used as the oxidoreductase.

The content of the oxidoreductase used in the present invention is not specifically limited and an appropriate content can be suitably chosen by those skilled in the art. For example, when GOD is used, the content of GOD is preferably about 0.1 to about 5 units per biosensor. When a combination of ChOD and ChE is used, the content of ChOD is preferably about 0.1 to about 5 units per biosensor and the content of ChE is preferably about 0.1 to about 5 units per biosensor. The term "1 unit" herein refers to an amount of oxidoreductase required for oxidizing 1 $\mu$mol of biochemical substrate to be quantitated in one minute.

The reaction layer may further contain at least one of hydrophilic polymers. Examples of the hydrophilic polymer include cellulose derivatives such as carboxy methyl cellulose (hereinafter, referred to as CMC), hydroxyethyl cellulose, hydroxypropyl cellulose, methyl cellulose, ethyl cellulose, ethyl hydroxy cellulose and carboxymethyl ethyl cellulose; polyvinyl pyrrolidone; polyvinyl alcohol; gelatin or its derivatives; acrylic acid or its salts; methacrylic acid or its salts; starch or its derivatives; and maleic anhydride or its salt. In particular, CMC is preferred.

When the above-mentioned ferricinium ion is employed as the electron acceptor, ferrocene is produced during sequential enzyme reactions. Since the ferrocene generally has low water-solubility, the produced ferrocene molecules deposit on the reaction layer due to water contained in a sample liquid. Thus, the reaction layer used in the present invention preferably contains at least one of surfactant. Examples of the surfactant include refined lecithin derived from soybean, octyl thioglucoside, sodium cholate, dodecyl-β-maltoside, sodium deoxycholic acid, sodium taurodeoxycholate, Triton-X (registered trademark), Lubrol PX (registered trademark), DK-ester (registered trademark), BIGCHAP (registered trademark) and DeoxyCHAP (registered trademark). Specifically, the refined lecithin and the octyl thioglucoside are preferred.

According to the present invention, a lecithin layer containing the above-mentioned refined lecithin may be further provided on the reaction layer. In the case where the lecithin layer is provided on the reaction layer, a sample liquid can be easily supplied to the reaction layer.

Hereinafter, a preferred embodiment of a method for producing a biosensor according to the present invention will be described with reference to FIGS. 1 and 2.

First, a conductive material such as silver paste is printed on an insulating substrate 1 by screen printing to form leads 2 and 3. Then, another conductive material containing a resin binder is printed on the insulating substrate 1 to form a working electrode 4 which makes contact with the lead 2.

Then, insulating paste is printed on the insulating substrate 1 to form an insulating layer 6. The insulating layer 6 covers the peripheral portion of the working electrode 4, so as to expose a fixed area of the working electrode 4. As is shown in FIG. 1, the insulating layer 6 also covers part of the leads 2 and 3. Around the working electrode 4 is formed a ring-shaped counter electrode 5 out of a conductive material containing a resin binder. The counter electrode 5 is in contact with the lead 3. In this manner, an electrode system 13 including the working electrode 4 and the counter electrode 5 is formed on the insulating substrate 1.

Alternatively, the biosensor according to the present invention may be provided with a three-electrode system including a reference electrode (not shown) in addition to the working electrode 4 and the counter electrode 5 formed on the insulating substrate 1. The three-electrode system provides stable response current, thereby further stabilizing the measurement accuracy.

A reaction layer 7 may be formed on the insulating substrate 1 as follows:

An aqueous solution containing the hydrophilic polymer is dropped and dried on the electrode system 13 to form a hydrophilic polymer layer. On the other hand, predetermined amounts of the oxidoreductase and the ferrocene electrolyte are dissolved in water. Preferably, a few drops of surfactant are added to this aqueous solution. Then, the obtained aqueous solution containing the oxidoreductase and the ferrocene electrolyte is added dropwise on the hydrophilic polymer layer. As a result, the hydrophilic polymer is dissolved in the aqueous solution. Then, the dissolved hydrophilic polymer layer is dried so that the reaction layer 7 is formed which is a hydrophilic polymer layer incorporating an oxidoreductase and an electron acceptor. Since the incorporation of the oxidoreductase and the electron acceptor (i.e., ferricinium ion) into the hydrophilic polymer layer does not require further steps such as stirring, only the hydrophilic polymer exists at the interface between the reaction layer 7 and the electrode system 13. In other words, since the oxidoreductase and the electron acceptor do not make contact with the surface of the electrode system 13, inactivation of the surface of the electrode system 13 can be avoided which is caused by adsorption of protein on the surface.

In the case where the hydrophilic polymer layer is not used, an aqueous solution containing oxidoreductase and ferrocene electrolyte is added dropwise and dried directly on the electrode system 13.

For repeated application of the biosensor, the oxidoreductase and the ferrocene electrolyte may be immobilized on the hydrophilic polymer layer through crosslinking with glutaraldehyde or immobilized on the hydrophilic polymer layer together with a polymeric material such as nitrocellulose or a conventional ion-exchange membrane.

Figure 2:
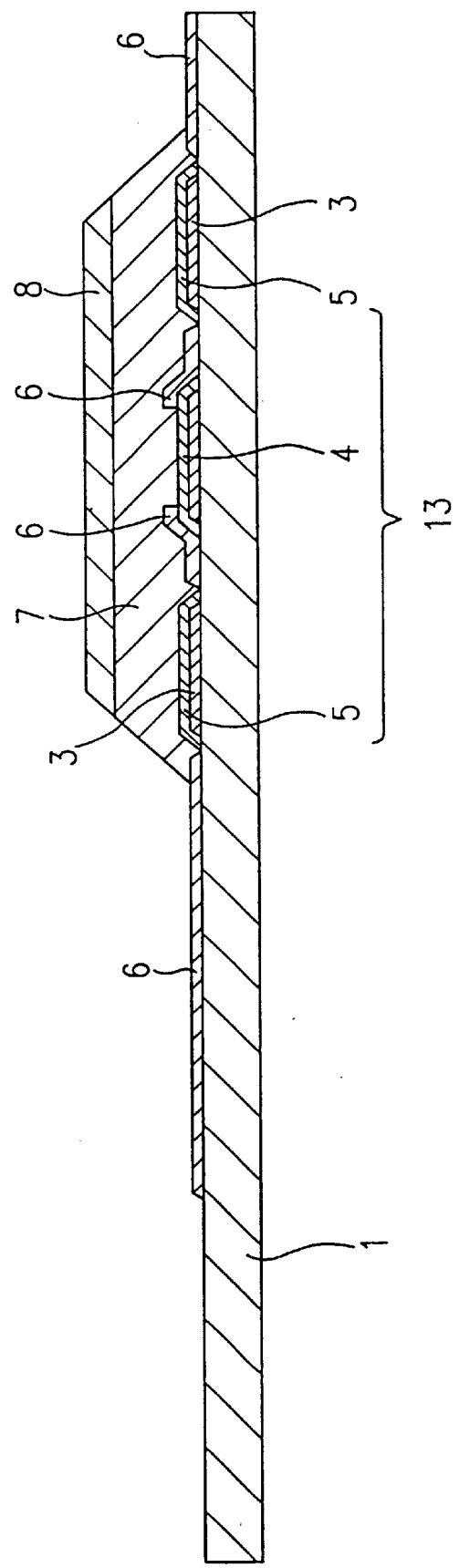
FIG. 2 is a schematic cross-sectional view showing a biosensor according to an example of the present invention in which a reaction layer is disposed on an insulating substrate.

As shown in FIG. 2, the reaction layer 7 is formed so as to cover the whole electrode system 13.

Then, if necessary, a predetermined amount of solution of refined lecithin in an organic solvent such as toluene is spread and dried on the reaction layer 7 to form a lecithin layer 8. Finally, as shown in FIG. 1, spacer 10 provided with a sample supply path 12 and a cover 9 provided with a hole 11 are disposed in this order above the insulating substrate 1 by a known method. Thus, the biosensor according to the present invention is produced.

A concentration of a biochemical substrate included in a sample liquid is quantitated by using the biosensor according to the present invention, for example, in the following manner.

First, a sample liquid containing a biochemical substrate is added to a reaction layer 7 directly or via the sample supply path 12. The reaction layer 7 is dissolved by the sample liquid. After a predetermined period of time, a predetermined level of pulse voltage (e.g., +0.5 V) is anodically applied to the working electrode 4 on the basis of a voltage at the counter electrode 5. The value of the resultant response current is measured in a known manner. Then, the response current value is converted into a concentration value of the biochemical substrate by using a calibration curve which represents the relationship between the concentration and the response current value of a biochemical substrate. The calibration curve is obtained in advance by measuring known concentrations of the biochemical substrate.

Hereinafter, a mechanism for obtaining response current value using the biosensor according to the present invention will be described.

For example, in the case where a sample liquid contains glucose as a biochemical substrate, GOD is used in the reaction layer 7. When the sample liquid is contacted with the reaction layer 7, the reaction layer 7 is dissolved by the sample liquid and the glucose in the sample liquid is oxidized by the GOD, thereby producing gluconic lactone. At this point, electrons generated through an oxidize reaction of the glucose reduce ferricinium ions existing in the reaction layer 7 into ferrocene. When the above-mentioned pulse voltage is applied to the working electrode, an oxidation current results which oxidizes the ferrocene. The amount of the oxidation current is measured as a reaction current value which is proportional to the concentration of glucose existing in the sample liquid.

In the case where a sample liquid contains cholesterol ester and cholesterol as biochemical substrates, ChE and ChOD are used in the reaction layer 7. When the sample liquid is contacted with the reaction layer 7, the reaction layer 7 is dissolved by the sample liquid and the cholesterol ester in the sample liquid is converted into cholesterol by ChE. Then, all of the cholesterol in the sample liquid is oxidized by ChOD, thereby producing cholestenone. At this point, electrons generated through an oxidizing reaction of the cholesterol reduce ferricinium ions existing in the reaction layer 7 into ferrocene. When the above-mentioned pulse voltage is applied to the working electrode, an oxidation current results which oxidizes the ferrocene. The amount of the oxidation current is measured as a reaction current value which is proportional to the total concentration of the cholesterol ester and cholesterol existing in the sample liquid.

Accordingly, the concentration of a biochemical substrate included in a sample liquid can be quantitated by the biosensor according to the present invention. Furthermore, since ferricinium ion used as an electron acceptor has a second-order reaction velocity faster than that of the ferricyanide ion used conventionally, the biosensor according to the present invention is capable of quantitating the concentration of the biochemical substrate in the sample liquid with accuracy and speed.

The biosensor according to the present invention can be effectively used for quantitating the concentration of the biochemical substrate included in biological samples such as whole blood, plasma, serum and urine, materials used in food industry and product thereof (e.g., fruit juice), or the like.

EXAMPLES

Hereinafter, the present invention will be described by way of illustrative examples with reference to the accompanying drawings. The present invention, however, is not limited to the following examples. In the accompanying drawings, same reference numerals designate same component and the description thereof is partially omitted for the sake of simplification.

Example 1

A glucose sensor was produced as follows as an example of a biosensor according to the present invention.

As shown in FIG. 1, silver paste was printed by screen printing on an insulating substrate 1 made of polyethylene terephthalate to form leads 2 and 3. Then, conductive carbon paste containing a resin binder was printed on the insulating substrate 1 to form a working electrode 4. The working electrode 4 was formed so as to be in contact with the lead 2.

Next, insulating paste was printed on the insulating substrate 1 to form an insulating layer 6. The insulating layer 6 covered the peripheral portion of the working electrode 4, so as to expose a fixed area of the working electrode 4. Moreover, conductive carbon paste containing a resin binder was printed on the insulating substrate 1 to form a ring-shaped counter electrode 5 so that the ring-shaped counter electrode 5 was in contact with the lead 3.

Then, an aqueous solution containing GOD and ferrocenium hexafluorophosphate (produced by Aldrich Inc.) was added and dried on the electrode system 13 (i.e., the working electrode 4 and the counter electrode 5) to form a reaction layer 7. A toluene solution containing lecithin was added dropwise on the reaction layer 7 to spread over the entire surface of the reaction layer 7 and dried to form a lecithin layer 8. A spacer 10 and a cover 9 were adhered in this order on the lecithin layer 8, thereby producing the glucose sensor.

3 μl of 30 mg/dl aqueous glucose solution was added to the above-described glucose sensor via a sample supply path 12 in the spacer 10. The sample liquid reached as high as the height of the hole 11 provided in the cover 9 and dissolved the reaction layer 7. Then, 60 seconds after the addition of the sample liquid, a pulse voltage of +0.5 V on the basis of a voltage at the counter electrode 5 was anodically applied to the working electrode 4. A response current value was measured 5 seconds after the voltage application.

Furthermore, response current values were measured with regard to aqueous glucose solutions of 45 mg/dl and 90 mg/dl, respectively in the same manner as described above by using a fresh glucose sensor for each measurement. The thus-obtained response current values were proportional to the respective concentrations of the aqueous glucose solutions.

Example 2

A glucose sensor was produced in the same manner as described in Example 1 except for using ferrocenium tetrafluoroborate (produced by Aldrich Inc.) instead of the ferrocenium hexafluorophosphate. By using this glucose sensor, response current values were measured for aqueous glucose solutions having the same concentrations as those described in Example 1 in the same manner as described in Example 1. The obtained response current values were proportional to the respective concentrations of the aqueous glucose solutions.

Example 3

An electrode system 13 was formed on an insulating substrate 1 in the same manner as described in the Example 1.

Then, an aqueous solution containing 0.5% by weight of CMC was added dropwise on the electrode system 13 (i.e., working electrode 4 and the counter electrode 5) and dried to form a CMC layer. An aqueous solution containing GOD and ferrocenium hexafluorophosphate was added dropwise and dried on the CMC layer to form a reaction layer 7. Furthermore, a toluene solution containing lecithin was added dropwise on the reaction layer 7 to spread over the entire surface of the reaction layer 7 and dried to form a lecithin layer 8. A spacer 10 and a cover 9 were adhered in this order on the lecithin layer 8, thereby producing the glucose sensor.

3 μl of 30 mg/dl aqueous glucose solution was added as a sample liquid to the above-described glucose sensor via a sample supply path 12 in the spacer 10. The sample liquid reached as high as a height of a hole 11 provided in the cover 9 and dissolved the reaction layer 7. Then, 60 seconds after the addition of the sample liquid, a pulse voltage of +0.5 V on the basis of a voltage at the counter electrode 5 was anodically applied to the working electrode 4. A response current value was measured 5 seconds after the voltage application.

Furthermore, response current values were measured with regard to glucose aqueous solutions of 45 mg/dl and 90 mg/dl, respectively, in the same manner as described above by using a fresh glucose sensor for each measurement. The thus-obtained response current values were proportional to the respective concentrations of the aqueous glucose solutions.

Example 4

A glucose sensor was produced in the same manner as described in Example 3 except for using ferrocenium tetrafluoroborate instead of the ferrocenium hexafluorophosphate. By using this glucose sensor, response current values were measured in the same manner as described in Example 3 for aqueous glucose solutions having the same concentrations as those described in Example 3. The obtained response current values were proportional to the respective concentrations of the aqueous glucose solutions.

Example 5

A glucose sensor was produced in the same manner as described in Example 3 except that refined lecithin derived from soybean (produced by SIGMA Chemical Co.) was added as a surfactant to the aqueous solution containing GOD and ferrocenium hexafluorophosphate. This aqueous solution was added dropwise on the CMC layer. By using this glucose sensor, response current values were measured in the same manner as described in Example 3 for aqueous glucose solutions having the same concentrations as those described in Example 3. The obtained response current values were proportional to the respective concentrations of the aqueous glucose solutions.

Example 6

A glucose sensor was produced in the same manner as described in Example 3 except that ferrocenium tetrafluoroborate was used instead of ferrocenium hexafluorophosphate and that refined lecithin derived from soybean was added as a surfactant to the aqueous solution containing GOD and ferrocenium tetrafluoroborate. This aqueous solution was added dropwise on the CMC layer. By using this glucose sensor, response current values were measured in the same manner as described in Example 3 for aqueous glucose solutions having the same concentrations as those described in Example 3. The obtained response current values were proportional to the respective concentrations of the aqueous glucose solution.

Example 7

An electrode system 13 was formed on an insulating substrate 1 in the same manner as described in Example 1.

Then, an aqueous solution containing 0.5% by weight of CMC was added dropwise and dried on the electrode system 13 (i.e., the working electrode 4 and the counter electrode 5) to form a CMC layer. Octyl thioglucoside was added as surfactant to an aqueous solution containing ChE, ChOD and ferrocenium hexafluorophosphate. The obtained aqueous solution was added dropwise and dried on the CMC layer to form a reaction layer 7. Furthermore, the toluene solution containing lecithin was added dropwise on the reaction layer 7 to spread over the entire surface of the reaction layer 7 and dried to form a lecithin layer 8. A spacer 10 and a cover 9 were adhered in this order on the lecithin layer 8, thereby producing the cholesterol sensor.

3 μl of standard solution containing 50 mg/dl of cholesterol and 150 mg/dl of cholesterol ester was added as a sample liquid to the above-described cholesterol sensor via a sample supply path 12 in the spacer 10. The sample liquid reached as high as a height of a hole 11 provided in the cover 9 and dissolved the reaction layer 7. Then, 180 seconds after the addition of the sample liquid, a pulse voltage of +0.5 V on the basis of a voltage at the counter electrode 5 of the electrode system 13 was anodically applied to the working electrode 4. A response current value corresponding to the total concentration of the cholesterol ester and cholesterol was measured 5 seconds after the voltage application.

Furthermore, response current values were measured with regard to a standard solution containing 300 mg/dl of cholesterol ester and 100 mg/dl of cholesterol and a standard solution containing 450 mg/dl of cholesterol ester and 150 mg/dl of cholesterol, respectively in the same manner as described above by using a fresh cholesterol sensor for each measurement. The thus-obtained response current values were proportional to the respective total concentrations of the cholesterol ester and cholesterol existing in the sample liquids.

Example 8

A cholesterol sensor was produced in the same manner as described in Example 7 except that ChE was not contained in the reaction layer 7. By using this cholesterol sensor, reaction current values were measured for the same standard solutions containing cholesterol ester and cholesterol, respectively. The thus-obtained response current values were only proportional to the respective concentrations of cholesterol in the standard solutions.

Example 9

A cholesterol sensor was produced in the same manner as described in Example 7 except for using ferrocenium tetrafluoroborate instead of the ferrocenium hexafluorophosphate. By using this cholesterol sensor, response current values were measured in the same manner as described in Example 7 for standard solutions containing cholesterol ester and cholesterol of the same concentrations as those described in Example 7. The obtained response current values were proportional to the respective total concentrations of cholesterol ester and cholesterol in the sample liquids.

Example 10

A cholesterol sensor was produced in the same manner as described in Example 7 except that ChE was not contained in the reaction layer 7 and ferrocenium tetrafluoroborate was used instead of the ferrocenium hexafluorophosphate. By using this cholesterol sensor, reaction current values were measured for the same standard solutions containing cholesterol ester and cholesterol, respectively. The thus-obtained response current values were only proportional to the respective concentrations of cholesterol in the standard solutions.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A biosensor comprising:
    an insulating substrate;
    an electrode system formed on the insulating substrate which comprises a working electrode and a counter electrode; and
    a solid phase reaction layer formed on the insulating substrate which contains a solid phase oxidoreductase and a solid phase ferrocene electrolyte as an electron acceptor, the solid phase reaction layer being formed over at least a portion of the working electrode or the counter electrode,
    wherein the ferrocene electrolyte consists of a ferricinium ion and a mono-anion, and wherein the ferricinium ion is provided in the biosensor together with the oxidoreductase upon dissolution of the reaction layer.

2. A biosensor according to claim 1, wherein the reaction layer further comprises at least one surfactant.

3. A biosensor according to claim 1, wherein the reaction layer further comprises at least one hydrophilic polymer.

4. A biosensor according to claim 1, wherein the oxidoreductase is selected from the group consisting of glucose oxidase; glucose dehydrogenase; lactate oxidase; lactate dehydrogenase; uricase; cholesterol oxidase; a combination of cholesterol oxidase and cholesterol esterase; a combination of glucose oxidase and invertase; a combination of glucose oxidase, invertase and mutarotase; and a combination of fructose dehydrogenase and invertase.

5. A method for quantitating the concentration of a biochemical substrate in a sample liquid by using a biosensor comprising an insulating substrate, an electrode system formed on the insulating substrate which has a working electrode and a counter electrode and a solid phase reaction layer provided on the insulating substrate which contains a solid phase oxidoreductase and a solid phase ferrocene electrolyte as an electron acceptor, the solid phase reaction layer being formed over at least a portion of the working electrode or the counter electrode, comprising the steps of:

adding the sample liquid to the reaction layer; and detecting a response current value by applying a voltage between the working electrode and counter electrode, wherein the ferrocene electrolyte consists of a ferricinium ion and a mono-anion, and wherein the ferricinium ion is provided in the biosensor together with the oxidoreductase upon dissolution of the reaction layer.

6. A method according to claim 5, wherein the reaction layer further comprises at least one surfactant.

7. A method according to claim 5, wherein the reaction layer further comprises at least one hydrophilic polymer.

8. A method according to claim 5, wherein the oxidoreductase is selected from the group consisting of glucose oxidase; glucose dehydrogenase; lactate oxidase; lactate dehydrogenase; uricase; cholesterol oxidase; a combination of cholesterol oxidase and cholesterol esterase; a combination of glucose oxidase and invertase; a combination of glucose oxidase, invertase and mutarotase; and a combination of fructose dehydrogenase and invertase.

9. A method according to claim 5, wherein the biochemical substrate is selected from the group consisting of glucose, cholesterol, lactic acid, uric acid and sucrose.

10. A biosensor comprising:

an insulating substrate;

an electrode system formed on the insulating substrate which comprises a working electrode and a counter electrode; and a solid phase reaction layer formed on the insulating substrate which contains a solid phase oxidoreductase and a solid phase ferrocene electrolyte as an electron acceptor, the solid phase reaction layer being formed over at least a portion of the working electrode or the counter electrode, wherein the ferrocene electrolyte consists of a ferricinium ion and a mono-anion, an enzymatic reaction occurs spontaneously between the oxidoreductase substrate, the oxidoreductase and the ferricinium ion of the ferrocene electrolyte, regardless of a potential of the electrode system, and wherein the ferricinium ion is provided in the biosensor together with the oxidoreductase upon dissolution of the reaction layer.

11. A biosensor according to claim 10, wherein the ferrocene electrolyte is selected from the group consisting of ferricinium hexafluorophosphate and ferricinium tetrafluoroborate.

12. A biosensor according to claim 10, wherein the reaction layer further comprises at least one surfactant.

13. A biosensor according to claim 10, wherein the reaction layer further comprises at least one hydrophilic polymer.

14. A biosensor according to claim 10, wherein the oxidoreductase is selected from the group consisting of glucose oxidase; glucose dehydrogenase; lactate oxidase; lactate dehydrogenase; uricase; cholesterol oxidase; a combination of cholesterol oxidase and cholesterol esterase; a combination of glucose oxidase and invertase; a combination of glucose oxidase, invertase and mutarotase; and a combination of fructose dehydrogenase and invertase.

* * * * *